United States Patent [19]

Klotzbach

[11] Patent Number: 5,012,535
[45] Date of Patent: May 7, 1991

[54] WHIRLPOOL TUB WITH AUTOMATIC PRE-FLUSHING OF THE SYSTEM

[75] Inventor: Manfred Klotzbach, Düren, Fed. Rep. of Germany

[73] Assignee: Hoesch Metall & Kunststoffwerk GmbH & Co., Kreuzau-Schneidhausen, Fed. Rep. of Germany

[21] Appl. No.: 443,204

[22] Filed: Nov. 30, 1989

Related U.S. Application Data

[62] Division of Ser. No. 284,546, Dec. 15, 1988, Pat. No. 4,901,926.

[30] Foreign Application Priority Data

Dec. 15, 1987 [DE] Fed. Rep. of Germany ....... 3742432

[51] Int. Cl.$^5$ ............................................ A61H 33/02
[52] U.S. Cl. ............................................ 4/541; 4/544
[58] Field of Search .................. 4/490, 492, 507, 509, 4/541, 542, 544; 128/66; 134/169 R, 169 C

[56] References Cited

U.S. PATENT DOCUMENTS

| | | | |
|---|---|---|---|
| 4,797,458 | 1/1989 | Guzzini | 4/542 |
| 4,829,607 | 5/1989 | Huse | 4/542 |
| 4,856,125 | 8/1989 | Dijkhuizen | 134/169 C |
| 4,857,112 | 8/1989 | Fränninge | 4/541 |

FOREIGN PATENT DOCUMENTS

| | | | |
|---|---|---|---|
| 3636328 | 5/1988 | Fed. Rep. of Germany | 4/542 |
| 0312953 | 4/1989 | Italy | 4/541 |
| 0338607 | 10/1989 | Italy | 4/542 |
| 8601100 | 2/1986 | World Int. Prop. O. | 4/542 |

Primary Examiner—Henry J. Recla
Assistant Examiner—Robert M. Fetsuga
Attorney, Agent, or Firm—Spencer & Frank

[57] ABSTRACT

A tub including a fluid system has a pump which includes a suction side and a pressure side; a nozzle for introducing a water-and-air mixture into the tub; the nozzle having a nozzle portion; a pressure line connecting the pressure side of the pump with the nozzle portion; a suction opening provided in a bottom region of the tub; and a suction line connecting the suction side of the pump with the suction opening. The fluid system further has a valve provided in the nozzle portion for cutting off fluid flow to the tub; an overflow line having a closable vent opening and being coupled to the suction side of the pump; a device for selectively allowing or blocking fluid communication between the overflow line and the suction line of the pump; and a supply source for introducing a cleaning agent at a location upstream of the nozzle as viewed in a direction of fluid flow therethrough.

11 Claims, 3 Drawing Sheets

WHIRLPOOL TUB WITH AUTOMATIC PRE-FLUSHING OF THE SYSTEM

This is a division of application Ser. No. 07/284,546 filed Dec. 15th, 1988 now U.S. Pat. No. 4,901,926.

BACKGROUND OF THE INVENTION

The invention relates to a tub having at least one nozzle, built into the vicinity of the tub wall for introducing a water-and-air mixture, which communicates via a pressure line with the pressure side of a pump, the intake side of which communicates via a pipeline with an intake opening in the vicinity of the bottom of the tub.

Tubs of this type, which as a rule can be installed like a standard bathtub, are used in such a way that for a "whirlpool bath", the tub is filled and emptied after the bath in the usual manner. Care must be taken when emptying the tub that the pump system pipelines, including the pump, are emptied as well, to prevent bacterial growth.

In relatively large-capacity tubs of this type, in which the tub or pool is kept filled over a relatively long period of time and is used several times before refilling, water-conditioning devices, in particular filters, are provided in the pipeline system so that germs can largely be prevented from forming in the water. In pools of this type as well, care must be taken that the pipeline system be emptied completely as well when the water is changed, so that when the pool is refilled, contamination of the freshly drawn water is avoided.

From German Patent 34 20 714, a whirlpool tub is known in which the pipeline system, via a system of level sensors and controllable valves, is equipped such that when it is filled, the entire pipeline system is first flushed with fresh water, so that any of the old water that may still remain is flushed out into the drain line and can no longer get into the water filling the tub when the swirl nozzle system, which functions by recirculation, is put into operation.

It has now been found that flushing with fresh water is no longer adequate over a relatively long period of time. The entire pipeline system that carries water must therefore be treated from time to time in a separate cleaning operation, in which a cleaning and/or disinfecting solution is poured into the tub along with the fresh water. Especially in whirlpool tubs used in private homes, either this additional operation is omitted completely or it is performed at such long time intervals that the danger that the water filling the tub will become contaminated by sources of bacteria in the pipeline system cannot be precluded.

The automatically closing nozzles known previously are not only complicated in their structure, because of the required pivotability of the nozzle body, but also have disadvantageous housing shapes, which do not permit complete emptying and/or satisfactory flushing with a cleaning agent. Moreover, a defined supply of the air via an air line protruding into the nozzle body is not possible, so that the previously known closable nozzle forms can admix air only in the suction mode, and the connection of an air compressor, or in other words an air supply that takes place independently of the flow through the nozzle, is not possible.

SUMMARY OF THE INVENTION

It is an object of the invention to embody a whirlpool tub such that each time the whirlpool bath is put into operation, both when it is refilled and when the swirl nozzle system is put into operation after the tub has been completely filled, a thorough flushing of the entire pipeline system, separately from the tub interior, can be performed, together with the addition of a cleaning and/or disinfecting agent.

The above and other objects are accomplished according to the invention by the provision of a fluid system, including: a pump which has a suction side and a pressure side; a nozzle for introducing a water-and-air mixture into the tub; the nozzle having a nozzle portion; a pressure line connecting the pressure side of the pump with the nozzle portion; a suction opening provided in a bottom region of the tub; and a suction line connecting the suction side of the pump with the suction opening; the improvement including:
 (a) a valve provided in the nozzle portion for cutting off fluid flow to the tub;
 (b) an overflow line having a closable vent opening; the overflow line being coupled to the suction side of the pump;
 (c) a device for selectively allowing or blocking fluid communication between the overflow line and the suction line of the pump: and
 (d) a supply source for introducing a cleaning agent at a location upstream of the nozzle as viewed in a direction of fluid flow therethrough.

The closability of the nozzles with respect to the interior of the tub makes it possible to flush the entire pipeline system separately, either with fresh water or with fresh water and a solution of cleaning agent and/or disinfecting agent, before each use of the swirl nozzle system. This can be done both upon refilling of the tub and when a tub is already completely filled. The overflow line between the nozzle and the suction line enables the circulatory flushing action to occur. If the overflow line is shut off from the suction line, the tub can be operated in the whirlpool mode with the nozzle opened. With both the tub and the pipeline system completely empty, the vent opening makes it possible to fill the pipeline system completely first, and in so doing to vent it, upon refilling the tub and/or when performing a separate cleaning operation, with the aid of the pump. The feeding of the cleaning and/or disinfecting agent, hereinafter referred to as the cleaning agent, is suitably effected upstream of the pump, so that satisfactory mixing of the cleaning agent with the water can be effected in the pump itself.

In another feature of the invention, the overflow line is closable with respect to the suction line by a preferably closable shutoff valve. In a further embodiment of the invention, the overflow line, at a location downstream of the nozzle, has a branch line which is closable with a closable shutoff valve and which discharges into the tub drain pipe. This embodiment makes possible the establishment of definite pressure conditions in the pipeline system for the various operating modes. The disposition of the branch line that can be shut off enables emptying the part of the overflow line located below the level of the tub completely as well. If the shutoff valve of the overflow line is completely opened and the shutoff valve of the branch line is not completely closed during cleaning, then, while simultaneously supplying fresh water, it is possible to remove some of the circulated water from the tub interior via the intake opening in the vicinity of the bottom of the tub, and then, once the cleaning operation is completed, to flush the pipeline system with fresh water and flush out all of the cleaning agent solution by simultaneously shutting off the overflow line from the suction line and completely opening the shutoff valve in the branch line. For whirlpool operation, the shutoff valve of the branch line is then closed as well, so that once the tub interior has been filled completely and with the nozzle now open, whirlpool operation can take place.

In a feature of the invention, the vent opening can be shut off with a shutoff valve which preferably a float valve, so that once the overflow line has been completely vented, the pipeline system can be subjected to circulating water and/or a cleaning agent solution.

In another advantageous feature of the invention, the nozzle has a shutoff body which keeps the pressure line closed off from the tub interior at a pump pressure between zero and a first low pressure level and automatically opens if the first pressure level is exceeded. While the above described cleaning operation can also be performed using manually closable nozzles instead of the nozzle having the shutoff body, this feature permits automatic operation, particularly if, via a corresponding control circuit, the shutoff valve in the overflow line and in the branch line are also triggerable and are actuated as a function of the pressure in the pressure line, or as a function of a fill level in the interior, or via a timing program. It is particularly advantageous if, as in a further feature of the invention, a pump of variable and preferably infinitely regulatable rpm is provided, which in combination with a level sensor switches the pump drive motor so that, when a minimum fill level in the tub is exceeded, a pumping capacity is used that results in a pump pressure lower than the first pressure level. This assures that, with a nozzle that opens automatically as a function of pressure, and with correspondingly opened shutoff valves in the overflow line and/or branch line, the fluid carried in the pipeline system via the pump cannot enter the tub interior.

While it is in principle possible to connect the pipeline system to the tub interior via a separate intake opening, a preferred embodiment of the invention provides that the intake opening of the suction line that communicates with the tub interior is disposed in a chamber-like tub drain fitting, in which the tub drain opening drains into the chamber-like tub drain fitting and the tub plug is disposed below the mouth of the intake line, the overflow line discharges above the tub plug, and the branch line discharges below the tub plug into the tub plug fitting. This makes it possible to combine the drain opening, which is necessary in any case, with the intake opening of the pump suction line, and at the same time to combine the overflow line, or its branch line, selectively with either the suction line or the drainpipe in one fitting. By disposing the mouth of the intake line of the overflow line in the chamber-like tub drain fitting at a location above that of the tub plug, it is also possible, given a suitable embodiment of the relevant flow cross sections, to flush the pipeline system thoroughly with a cleaning agent solution as well, without requiring an additional plug for the intake opening and without this cleaning agent being capable of entering into the tub interior. This can be assured if, when the shutoff valve is slightly open, the pump draws fluid in an amount via the suction line from the chamber-like connection fitting such that, in addition to the quantities of fluid received from the overflow line, a small quantity of fluid is also drawn from the tub interior via the intake opening.

The invention also relates to an automatically closing nozzle for introducing a mixture of water and air into a tub, in particular a tub of the type described above. This nozzle has a support ring, by way of which a prechamber communicating with the pressure line is firmly joined to the tub wall and with which a retaining ring is releasably connected, and wherein a nozzle body embodied as a ball is pivotably held in the support ring. The nozzle body has a bore that communicates with the prechamber, and the mouth of an air supply line protrudes into the bore externally of the tub.

To overcome the problems of the prior art set forth hereinabove, the invention provides that the retaining ring is embodied as a plunger and is retained axially displaceably in the support ring and is supported on its side remote from the prechamber via compression spring elements; that the bore of the nozzle body has, on its end oriented toward the mouth of the air supply line, an annular sealing element circumscribing an entrance to the bore; and that the outside of the mouth of the air supply line has an external surface portion which is spherical, the nozzle body being urged against this spherical surface portion by the compression spring elements such that the sealing element seats against it. A nozzle embodied in this way, having a rigid air supply line protruding into the nozzle body, can be closed independently of the pivoted position of the spherical nozzle body, when no pressure is applied to the prechamber. Only when the pressure applied to the prechamber creates a force on the plunger that is greater than the closing force of the compression spring elements, does the sealing element lift from the spherical face of the mouth of the air supply line and free the connection between the prechamber and the interior of the tub. The closing force of the compression spring elements is designed such that it is higher than the plunger force that corresponds to the pressure in the prechamber during the flushing operation. Particularly in the case where an only slightly deformable material is used for the annular sealing element, it is advantageous for the center of the spherical face of the mouth of the air supply line to coincide with the center of the spherical body when the sealing element is in contact with the spherical face.

In a further feature of the invention, the ends of the compression spring elements which are remote from the prechamber are braced against an adjusting ring which is axially adjustable with respect to the mouth of the air supply line. With the aid of such an adjusting ring, it is possible on the one hand to vary the flow cross section of the nozzle for control of the flow of water through the nozzle independently of the pumping capacity of the pump, so that even when pumps not having a regulatable pumping capacity are used, it is possible to vary the quantity of water emerging through the nozzle. On the other hand, it is possible to close the nozzle completely by hand as well, so that the nozzle body with its annular sealing element is pressed firmly against the spherical outside face of the mouth of the air supply line, so that even when a high pressure prevails in the prechamber the nozzle does not open. This is particularly important for nozzles of tubs which permit pre-flushing of the system, of the type according to the invention. During normal operation and with a nozzle that automatically opens if the first pressure level is exceeded, a solution of cleaning agent can be pumped only "gently", in other words with a low flow velocity through the pipeline system, without causing opening of the nozzle. When the nozzle is closed by movement of the adjusting ring, it is possible to flush out the pipeline system with the full pump power, so that instead of or in addition to the chemical action of the cleaning agent, a mechanical cleaning action can be attained via high flow velocities. In an advantageous embodiment, the adjusting ring is accessible from the interior of the tub and includes at least one handle element.

In another advantageous feature of the invention, the adjusting ring and the retaining ring are joined together in a manner fixed against relative rotation but such that they are axially displaceable relative to one another. This arrangement has the advantage that, upon an actuation of the adjusting ring, no relative rotational movement between the adjusting ring and the retaining takes place, so that the compression spring elements, upon an adjustment, are not strained in the transverse direction, therefore precluding jamming or tilting thereof.

In still another feature of the invention, the space surrounding the spring elements is vented. This has the advantage that the automatic closing and opening function of the nozzle is maintained, even if after a relatively long period of operation the plunger seals were to become leaky so that the equilibrium pressure will not build up in the space surrounding the spring elements, so that the spring elements would keep the plunger in the closing position even at operating pressure. Thus via the vent opening, not only can the air volume in this space escape, but any fluid that has entered it can escape as well, so that when the prechamber is pressurized, an unequivocal pressure difference can always exist between the prechamber and the space surrounding the spring element.

In a further advantageous embodiment of the invention, the plunger is provided, on an end thereof which is oriented toward the prechamber, with a scraper, which in the closing position of the nozzle protrudes into the prechamber. By means of a scraper of this kind, which may also be part of the plunger seal, it is assured that when the system is depressurized lime deposits that form on the associated inner cylindrical face of the support ring are mechanically removed, to facilitate reciprocation of the plunger in the support ring even after a long period of operation.

In nozzles for use with tubs having the pre-flushing of the system according to the invention, a further feature of the invention is that the prechamber, on its upper side, has a connection piece for connection to an overflow line. This makes it possible to vent the prechamber completely when the cleaning solution is introduced, with the action of the pump causing filling of the prechamber.

In a further advantageous embodiment of the invention, the prechamber is provided on its lower side with an inlet opening which has at least two branches which are preferably oriented at right angles from one another. This arrangement has the advantage that for smaller tubs, in which only two nozzles per tub side are provided, the nozzles can be disposed at the same height, and the pressure line connecting the two nozzles together as well as the pressure line extending from the pump to the first nozzle, when viewed in the flow direction, can be laid practically without a slope, so that when the system is emptied the liquid can flow back out of the prechamber to the pump. This makes installation considerably simpler, because it becomes largely unnecessary to provide additional fittings.

In another advantageous feature of the nozzle according to the invention, the air supply line protrudes at an angle extending from top to bottom through the prechamber into the bore of the nozzle body. This arrangement has the advantage that the part of the air supply line located in the vicinity of the nozzle can also be completely emptied when the system is emptied.

The invention also relates to a tub drain fitting for tubs with system pre-flushing, in particular for a tub of the type according to the invention that can be connected to the drain opening of the tub. This tub drain fitting includes a flow chamber disposed beneath the bottom of the tub, the flow chamber having an upper opening that terminates in the form of a drain opening into the tub interior, and has a lower opening that discharges into the drain pipe and is closable with a valve body which is externally actuatable, the flow chamber above the valve body having two preferably diametrically opposed flow openings, wherein one of the flow openings is connectable to an inflow line and the other is connectable to a suction line. A tub drain fitting embodied in this way has the advantage that the tub drain opening also serves as an intake opening for the suction line of the pump, so that when the inflow line is closed, water can be carried out of the tub interior via the pump through the nozzles in a circulating loop (whirlpool operation). When the inflow line is opened, then depending on the relative sizes of the cross sections of the intake line on the one hand and the inflow line on the other, the inflow line preferably having a smaller cross section, the quantity of fluid flowing in from the inflow line is introduced in jet form directly into the intake line, so that an overflow of the fluid from the inflow line into the tub interior is avoided. Instead, a slight drag flow is generated, which carries some of the fluid along with it out of the tub itself via the suction line. During a flushing operation, in particular during a flushing operation using a solution including a cleaning agent, the cleaning agent solution is prevented from getting into the tub interior.

In another embodiment of the invention, the opening connectable to the inflow line has a pipe extension protruding into the flow chamber toward the other opening. As a result, the quantity of fluid arriving from the inflow line operates in the manner of a jet pump with respect to the drain opening of the tub.

In an advantageous embodiment of the invention, the opening communicating with the tub interior communicates via a pipe insert with the drain opening located beneath it, the pipe insert having a smaller diameter than the inside diameter of the flow chamber, and the wall of the pipe insert, on the side of the opening of the flow chamber communicating with the suction line, is provided with at least one flow opening. In this arrangement, the opening of the flow chamber serving as the drain opening of the tub is shielded from the inflow line, so that the water flowing from the inflow line is prevented from flowing directly into the tub interior. At the same time, the pipe insert, with its flow openings oriented toward the opening of the suction line, prevents the unhindered passage of the water from the tub interior into the suction line, so that a normal whirlpool operation is assured.

The invention will be described in greater detail below with reference to an embodiment which is illustrated in the drawings.

DESCRIPTION OF THE PREFERRED EMBODIMENT

Figure 1:
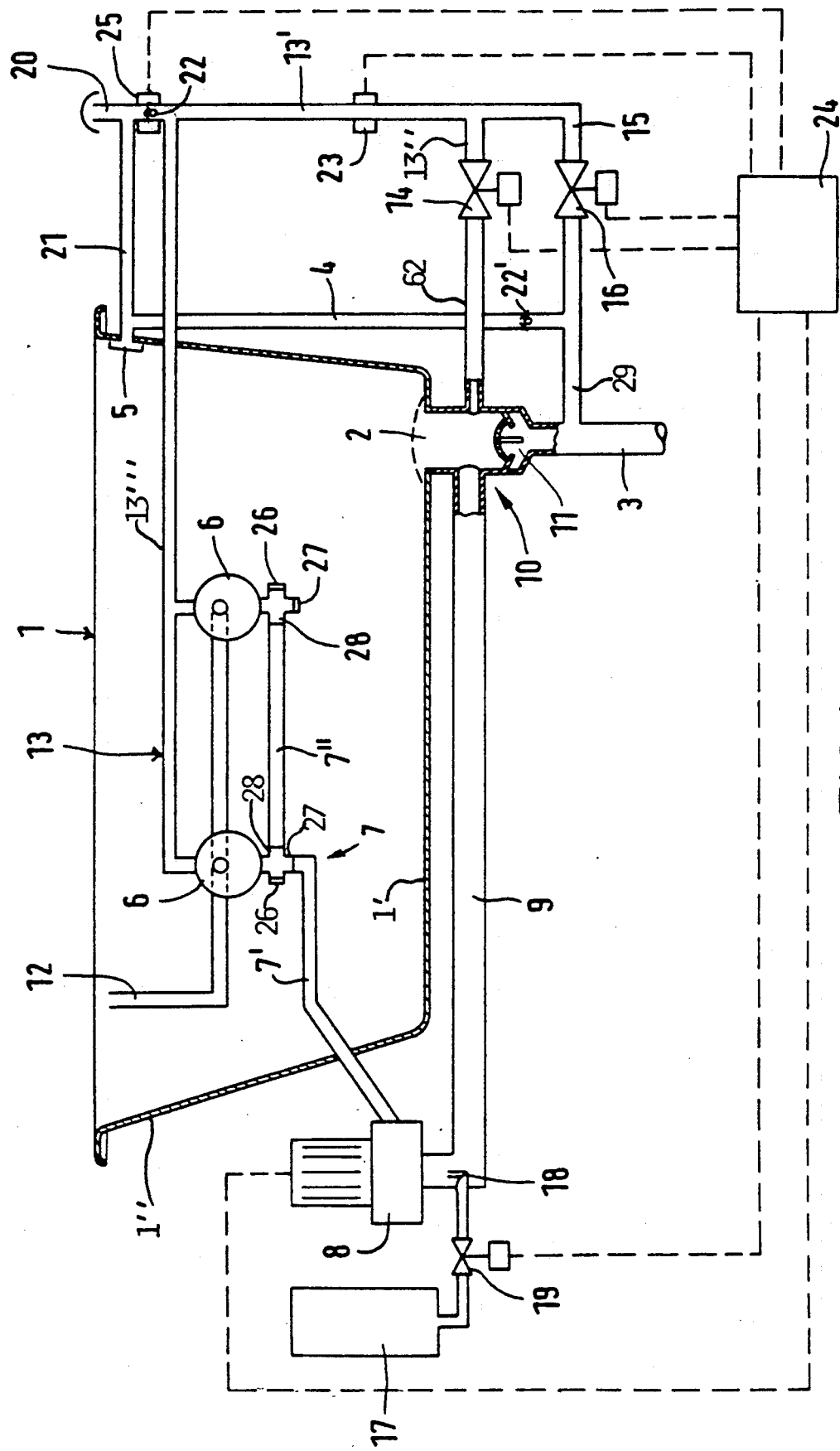
FIG. 1 is a schematic view of a whirlpool tub and the associated a pipeline system in accordance with the invention.

A whirlpool tub 1 is schematically shown in FIG. 1 having the form of a relatively large bathtub which is provided in a conventional manner with a drain opening 2 in the vicinity of a tub bottom 1', the drain opening 2 communicating with a drainpipe 3. A tub drain 5 also communicates in a conventional manner with the drainpipe 3 via a pipeline 4.

On each of its two opposed long sides, the tub 1 has two nozzles 6, through which a mixture of water and air can be introduced in jet fashion into the tub interior when the bathtub is filled. The nozzles 6, which are described hereunder in further detail with reference to FIG. 2, have pivotable nozzle bodies, so that the jet direction is freely adjustable within predetermined limits.

A pressure line 7, having horizontal portions 7' and 7", connects the nozzles 6 with the pressure side of a pump 8, which in turn communicates via a suction line 9 and a drain fitting 10 with the drain opening 2. The drain opening 2 serves as an intake opening for the pump 8 to provide recirculation of water in the tub 1. The drain fitting 10 has a valve body 11 therein which is closable to prevent fluid flow into the drainpipe 3, the valve body 11 being externally actuatable. The pump 8 is disposed horizontally, such that its intake opening is oriented downwardly, so that when the pump is stopped and the valve body 11 is opened, the pressure line 7 can drain through the pump 8 into the suction line 9, which drains into the drainpipe 3 until it is completely empty.

The nozzles 6 also communicate with an air supply line 12, through which the nozzles 6 draw air, via either the draft action of the water flowing into the tub space or via a connected compressor (not shown), so that air can be introduced along with the water into the tub 1 in the form of a jet-like water-and-air mixture injected by the nozzles 6. The air intake opening of the air supply line 12, during a suction operation, and alternatively the air compressor if used, are preferably adjustable such that the quantity of air introduced to the nozzles can be regulated.

Figure 2:
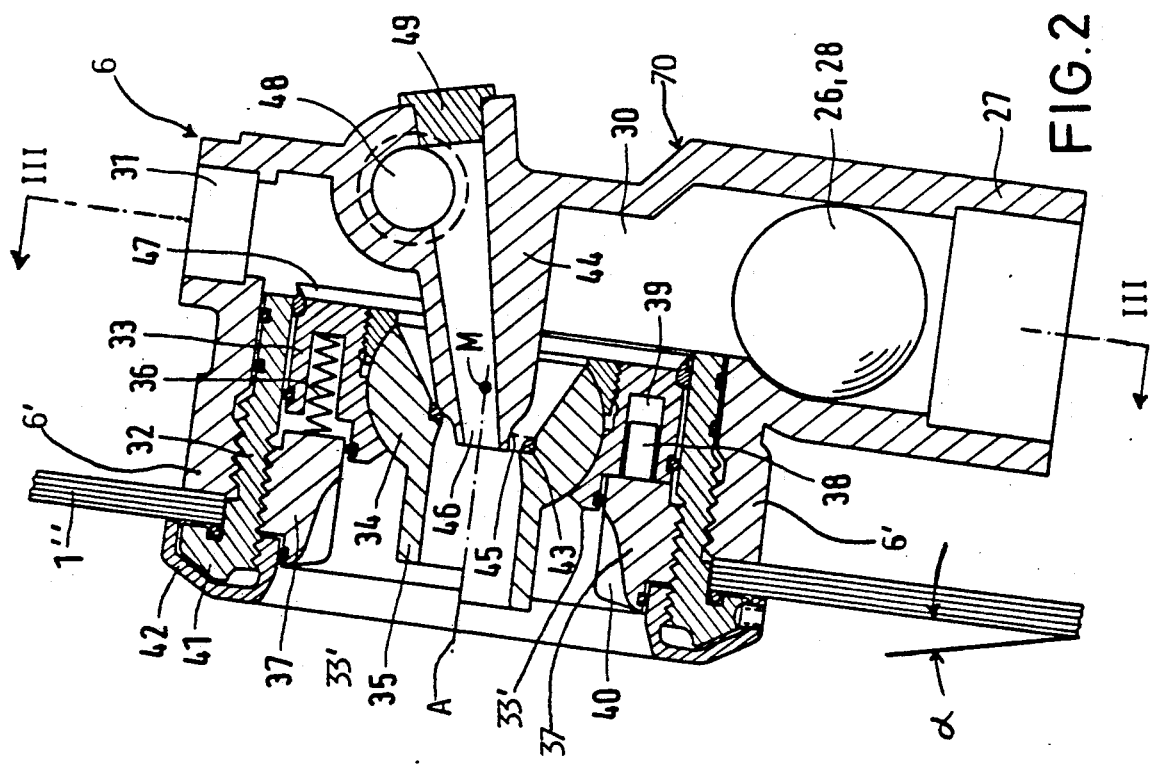
FIG. 2 is a side elevational view of a nozzle for the tub of FIG. 1.

The pressure line 7 discharges upwardly into a prechamber 30 of the nozzles 6, shown in FIG. 2, that is disposed on the outside of the tub 1. The prechamber 30 is connected at its top to an overflow line 13. The overflow line 13 is described in further detail hereunder in conjunction with FIGS. 2 and 3.

The overflow line 13 has a horizontal section 13''' connected to a vertical section 13' which supplies both a discharge section 13" and a branch line 15. The discharge section 13" is connected to a shutoff valve 14 which, when open, enables discharge of liquid into the drain fitting 10 above the valve body 11 via a drain line 62. The branch line 15 is likewise closable with respect to th drain fitting 10 or the drainpipe 3 via a shutoff valve 16 which, when open, enables discharge of liquid directly to the drainpipe 3. A supply container 17 is provided to supply a cleaning and/or disinfecting agent and is connected to the suction line 9 via a shutoff valve 19 and a supply line 18.

The overflow line 13 also has a vent fitting 20, preferably extending upwardly as far as the height of the rim of the tub 1 and forming a vent opening for the overflow line 13. Branching off from the vent fitting 20 is a transverse line 21 which communicates with the overflow line 4. An automatic valve, for instance a float valve 22, is disposed in the vertical section 13' of the overflow line 13 at a height above that of the horizontal section 13''' and below that of the transverse line 21 so that only relatively slight quantities of fluid, equivalent to leakage, can pass from the overflow line 13 into the pipeline 4 via the transverse line 21.

The vertical portion 13' of the overflow line 13 is connected to a level sensor 23, the control signal of which is sent to a control unit 24. The level sensor 23 is located at a height corresponding to a predetermined minimum fill height, for instance 10 cm, with respect to the tub bottom 1'. A further level sensor 25, which is also connected to the control unit 24, is provided in the vent fitting 20 above the float valve 22.

The signals supplied by the level sensors 23 and 25 to the control unit 24 are used to control the drive motor of the pump 8 in such a way that the pump 8 cannot be switched on until the minimum fill height, which is predetermined by the height of the level sensor 23, has been attained, and such that even then the pump 8 is controlled to have only a relatively low pumping capacity. Only when the operating fill height predetermined by the level sensor 25 is attained can the pump 8 be switched on with full pumping capacity.

The pipeline system is preferably controlled, as described in further detail below in conjunction with FIG. 2, so that when the nozzles 6 are closed, the shutoff valve 14 is open, and the shutoff valve 16 in the branch line is closed upon attainment of the minimum fill height predetermined by the level sensor 23, so that the pump 8 can pump fluid in a circulating loop which includes the pressure line 7, the overflow line 13 (including the horizontal section 13''', the vertical section 13' and the discharge section 13"), and the suction line 9. The drain fitting 10 here is embodied such that no fluid, or only slight quantities of fluid, can reach the suction line 9 from the interior of the tub 1 during operation of the circulating loop, as will be described in further detail below in conjunction with FIG. 4. Upon opening of the shutoff valve 19, a cleaning or disinfecting agent can then be added in metered fashion, so that a solution of cleaning agent can be circulated through the pipeline system, e.g. through the circulating loop. When the shutoff valve 16 is open, the solution flows through the branch line 15, the drain line 29, and the overflow line 13 without coming into contact with the tub interior.

If the shutoff valves 14 and 16, and optionally the shutoff valve 19 as well, are equipped with controllable operating drives, they also can be connected to the control unit 24, so that both the triggering of the pump 8 and the triggering of the shutoff valves 14 and 16, and optionally the shutoff valve 19, can be effected via the control unit 24 in accordance with a predetermined switching program. It is also possible in this respect for the shutoff valve 16 to be opened slightly during the cleaning operation, so that a partial flow of cleaning agent solution is always drained into the drainpipe 3, and corresponding quantities of fresh water from the tub interior or from a fresh water supply, can enter the suction line 9. After the completion of the cleaning procedure, the shutoff valve 16 is opened completely and the shutoff valve 14 is closed completely, so that, together with a simultaneous aspiration of fresh water from the interior of the tub 1 through the drain opening 2, the pipeline system carrying the water (comprising the suction line 9, the pressure line 7 and the overflow line 13), can be flushed completely with fresh water. After this flushing process is completed, the shutoff valve 16 is closed.

Since upon the beginning of the cleaning process the pump 8 functions only at a low pumping capacity, it is additionally possible to fill the pipeline system relatively slowly on the pressure side of the pump 8, so that the quantities of air contained therein (i.e., in the pressure line 7, each prechamber 30 of the nozzles 6, and the overflow line 13), can escape via the vent fitting 20. In this case, the pipeline system continues to be filled slowly until the overflow system is also completely filled, i.e. in this case until the vertical section of the overflow line 13 is also completely filled, whereupon the float valve 22 finally closes.

During the cleaning operation, the filling of the tub can be continued, because only when the operating fill height predetermined by the level sensor 25 is reached can the pump 8 be switched to full capacity. Via a corresponding locking circuit, (e.g. in the control unit 24,) it can be assured that only upon the closure of the shutoff valve 16, after the completion of the flushing with fresh water, is pump operation at full capacity possible. With manually closed nozzles 6, these nozzles must first be opened. With automatically closing nozzles, the very much higher pump pressure during whirlpool operation as compared with the cleaning operation is sufficient to open the nozzles.

In the inflow region, each of the nozzles 6 are provided with three connection fittings 26, 27, and 28, wherein the connection fillings 26 and 28 are aligned horizontally and the connection fitting 27 is oriented vertically, so that with the arrangement shown, a portion 7" of the pressure line 7 extending between the two nozzles 6 communicates with the horizontally aligned connection fittings 26 and 28, while a portion 7' of the pressure line 7, which is located between the pump 8 and the first of the nozzles 6 in the flow direction, is connected to the connection fitting 27 which points downwardly. This assures satisfactory drainage of the water when the pipeline system is emptied.

In FIG. 2, a particular embodiment for an automatically closing nozzle 6 is shown. The nozzle 6 includes a prechamber 30, having the horizontally extending connection fittings 26, 28 at a bottom portion thereof (also shown in FIG. 3) beneath which extends the vertically downwardly pointing connection fitting 27. On the top of the nozzle 6 is a connection fitting 31 for attachment to the portion 13''' of the overflow line 13. The prechamber 30 is secured to and sealed against the outside of a side tub wall 1" of the tub by a clamping collar 41 which has a sealing face contacting the side tub wall 1" and a generally cylindrical support ring 32 having an axis A which is engaged within an interior of a nozzle support wall 6' by a threaded connection. The side tub wall 1" extends outwardly from the interior of the tub 1 at an inclination of angle $\alpha$, for example, from the vertical, and therefore the central axis of the support ring 32 is also tilted from the horizontal at an angle $\alpha$. In the support ring 32 is disposed a retaining ring 33 which is embodied as an axially displaceable plunger and which has circumferentially arranged seals.

A nozzle body 34 is embodied as a ball-like portion having a center of curvature M, and which is pivotably retained in an annular portion 33' of the retaining ring 33. The nozzle body 34 has a tubular mouth 35 that can direct a jet of fluid into the tub interior.

The retaining ring 33 is biased toward the prechamber 30 via a plurality of compression spring elements 36 distributed generally uniformly in the radial direction about the axis A. An adjusting ring 37 is fastened within the support ring 32 by a threaded connection, and serves as an end stop for the retaining ring 33. The adjusting ring 37 also has at least one guide pin 38 which engages the inside of an axial bore 39 in the retaining ring 33, so that the retaining ring 33 is guided by the guide pin 38 during movement thereof in the axial direction relative to the adjusting ring 37. Since the adjusting ring 37 is retained in the support ring 32 via a threaded connection, the adjusting ring 37 and the retaining ring 33 can be rotated relative to each other about the common axis A, and can thereby be relatively axially displaced. As a result of the resilient spring coupling between the retaining ring 33 and the adjusting ring 37 formed by the springs 33, the axial play between the displaceable retaining ring 33 and the adjusting ring 37, as well as the spring biasing force (within certain limits), can be adjusted. The adjusting ring 37 is provided with a handle element 40 accessible from the inside of the tub, which is for instance in the form of a rib, and which can also be embodied as a recess. An ornamental cap 42 covers the clamping collar 41 of the support ring 32 and has an innermost cylindrical flange which serves as a limitation of the axial adjustment of the adjusting ring 37 in the direction toward the inside of the tub 1.

The nozzle body 34 has a bore therethrough which communicates with the prechamber 30 and widens in the axial direction toward the prechamber 30. An annular sealing element 43 is disposed adjacent an innermost diameter of the bore and is supported by the nozzle body 34 on the side of the bore which is oriented toward the prechamber 30. An air supply member 44 is oriented within the prechamber 30 in a generally axial direction relative to the axis A and, in the exemplary embodiment shown, is inclined slightly counterclockwise from the horizontal and extends into the bore of the nozzle body 34. The air supply member 44 has a mouth 46 which protrudes into the bore in the nozzle body 34 and has a tip having a generally spherical outer face portion 45 which cooperates with the annular sealing element 43 to form a seal. In an unpressurized state of the prechamber 30, the nozzle body 34 is pressed, along with its sealing element 43, against the outer face portion 45 via the compression spring elements 36. The interior of the bore of the nozzle body 34 contacts the outside face 45 of the mouth 46 at a contact surface of the nozzle body 34 which is formed as a generally spherical interior face portion mating with the outside face 45 so that the nozzle body 34 can be pivoted relative to the retaining ring 33 without causing the sealing element 4 to lift from the face 45 of the mouth 46. Therefore, in any arbitrary angular position of the nozzle body 34, the seal is maintained between the interior of the tub 1 and the prechamber 30.

As a result of the disposition of the retaining ring 33 relative to the nozzle body 34 with respect to the prechamber 30, any buildup of fluid pressure within the prechamber 30 effects a plunger force on the nozzle body 34 oriented counter to the force of the compression spring elements 36. The plunger force acting on the nozzle body 34 can overcome the closing force of the compression spring elements 36 only if the fluid is in excess of a predetermined pressure level. When this pressure level is exceeded, the nozzle body 34, together with its seal 43, are lifted away from the counterpart face 45 of the mouth 46, so that water supplied to the prechamber 30 can flow into the tub interior. For a pipeline system having a pre-flushable line system, the closing force of the compression spring elements 36 can be adjusted by rotation of the retaining ring 33 relative to the support ring 32, such that at a relatively small minimum pumping capacity of the associated pump 8, the nozzles 6 are securely closed, and such that the nozzles 6 are securely opened only after the very much higher pumping capacity required for whirlpool operation has been initiated.

By rotation of the adjusting ring 37 relative to the support ring 32 to cause movement of the adjusting ring 37 in the direction of the prechamber 30, however, it is possible to suppress the pressure-dependent axial motion of the retaining ring 33 and to press the nozzle body 34 against the mouth 46, so that the pipeline system can be flushed thoroughly with the full pumping capacity of the pump 8, without discharge of the cleaning solution into the tub 1.

The retaining ring 33 includes an edge region having a scraper 47, which, when the fluid pressure is cut off, protrudes into the prechamber 30, so that lime deposits can be scraped off of the cylindrical interior face of the support ring 32 or cannot form there in the first place.

FIG. 2 illustrates the retaining ring 33, which moves as a unit with the nozzle body 34 and the tubular mouth 35 connected to it, in two positions thereof (split above and below the axis A) relative to the adjusting ring 37 and to the outside face 45 of the air supply member 44. The closed position is shown above the axis A, wherein the annular sealing element seats against the outside face 45. The open position is shown below the axis A, wherein the retaining ring is moved to the left relative to its closed position, until it abuts the adjusting ring 37.

Figure 3:
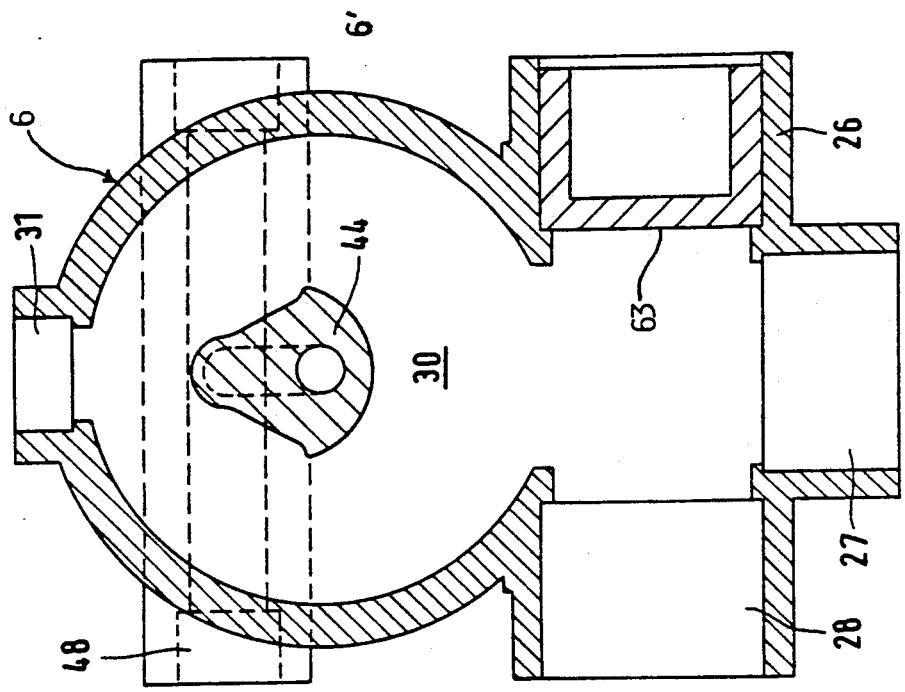
FIG. 3 is a side sectional view taken along the line III—III of FIG. 2.

Whenever the nozzle body 34 is resting sealingly on the mouth 46, communication between the tub interior and the prechamber 30 is interrupted. At the same time, water can flow into the air supply member 44 when the tub is filled. However, because the air supply member 44 is inclined, it is reliably emptied when the tub 1 is emptied. In the exemplary embodiment shown, the communication of the air supply member (not shown) with the air line 12 is effected by lateral connection fittings 48, so that the additional possibility of an axial connection remains, for example for connection of an air compressor (not shown). In the exemplary embodiment shown, however, the axial inflow connection is closed with a plug 49. As shown in FIG. 3, unnecessary connection fittings can be closed by a plug, for example the connection fitting 26 is closed as shown by the plug 63.

As FIG. 2 shows, the movable parts of the nozzle 6 are accessible at any time from the tub interior, without having to remove the arrangement from the tub 1. To this end, all that needs to be done is to loosen the ornamental cap 42 and then to remove the adjusting ring 37 along with the retaining ring 33 embodied as a plunger. The seals of the parts which are movable relative to one another can then be replaced, or the plunger element (the retaining ring 33) can be replaced.

Figure 4:
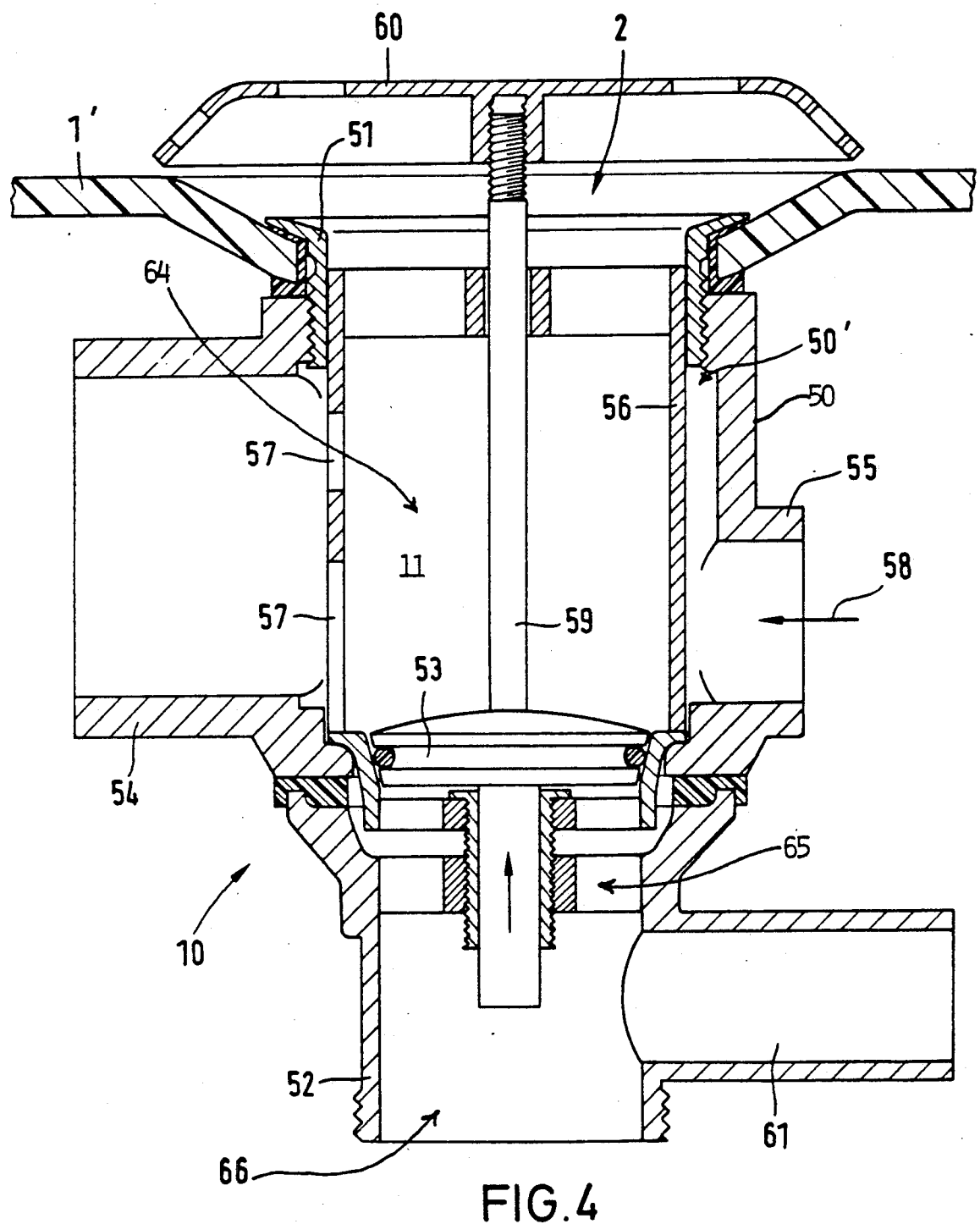
FIG. 4 is a side sectional view of a drain fitting for the pipeline system of FIG. 1.

In FIG. 4, an exemplary embodiment for the drain fitting 10 is shown. The drain fitting 10 has a body 50 which defines an upper chamber portion 64, a lower chamber portion 65, and a discharge connection portion 66. The upper chamber portion 64 includes a flow chamber 50', which is firmly connected via a clamping ring 51 to the drain opening 2 in the bottom of the tub 1. The flow chamber 50 has a connection fitting 52 on its lower end, with which it is connected to the drainpipe 3 (not shown in FIG. 4). A valve body 53 is disposed in the lower region of the flow chamber 50 and can be raised from the closed position, shown, into an open position via an opening mechanism (not shown).

The flow chamber has a flow opening member 54 having an opening therein of large diameter disposed above the plane of the valve body 53, and is in the form of a connection fitting, which is disposed diametrically opposite a second flow opening member 55, which is likewise in the form of a connection fitting. The flow opening member 55 has a flow opening having a smaller flow cross section than that of the flow opening member 54. The suction line 9 of the pump 8 is connected to the flow opening 54, and the overflow line 13 of the pipeline system described in conjunction with FIG. 1 is connected to the flow opening 55.

A pipe insert 56 is disposed in the body 50 and has a smaller diameter than the flow chamber 50' itself. The side of the pipe insert 56 which is oriented toward the flow opening 54 has a plurality of openings 57, while on the opposite side, oriented toward the flow opening 55, the pipe insert 56 has a completely closed wall. With suitable dimensioning of the openings 57, water is prevented from flowing in to the tub interior during the flushing process via the flow opening member 55 in the direction of the arrow 58.

The valve body 53 has an extension 59 on its top which is connected to a cover cap 60 provided with holes. When the valve body 53 of the drain fitting 10 is closed, the hole in the cover cap 60 serve as a means to connect the inflow opening in the flow opening member 55 to the suction line 9. When the valve body 53 is opened, the cover cap 60 is raised as well, so that a sufficient flow cross section for a rapid emptying process is available. The openings 57 in the pipe insert 56 are disposed such that the inflow lines communicating with the openings 55 and 54 ca likewise be emptied completely via the drain fitting 10. Below the valve body 53, a further flow opening 61, likewise in the form of a connection fitting, is provided, into which the branch line 15 discharges.

The present disclosure relates to the subject matter disclosed in German Application No. P 37 42 437.2, the entire specification of which is incorporated herein by reference.

It will be understood that the above description of th present invention is susceptible to various modifications, changes and adaptations, and the same are intended to be comprehended within the meaning and range of equivalents of the appended claims.

What is claimed is:

1. In a tub including a fluid system having a pump including a suction side and a pressure side; at least one nozzle for introducing a water-and-air mixture into the interior of the tub; the nozzle having a nozzle portion in communication with the pump; a pressure line connecting the pressure side of the pump with the nozzle; a suction opening provided in a bottom region of said tub; a closable tub drain fitting connected to the suction opening; and a suction line connecting the suction side of the pump with the suction opening; the improvement comprising:

(a) valve means provided in the portion of the nozzle in communication with the pump for cutting off fluid flow from the pump through the nozzle; said valve means being accessible from the interior of the tub;

(b) an overflow line having a closable vent opening; said overflow line being coupled to the suction side of the pump;

(c) means for selectively allowing or blocking fluid communication between said overflow line and the suction line of the pump; and (d) supply means for introducing a cleaning agent at a location upstream of said nozzle as viewed in a direction of fluid flow therethrough.

2. A tub as defined by claim 1, wherein said means for selectively allowing or blocking fluid communication between said overflow line and the suction line of the pump comprises a controllable shutoff valve.

3. A tub as defined by claim 1, further comprising:
a tub drainpipe connected to the closable tub drain fitting for discharging liquid from the fluid system;
a branch line connecting said overflow line to said tub drainpipe;
a controllable shutoff valve for selectively allowing or blocking fluid communication between said branch line and said tub drainpipe, said controllable shutoff valve being disposed in said branch line; and
said branch line being connected to said overflow line at a location downstream of the nozzle as viewed in a direction of fluid flow therethrough.

4. A tub as defined by claim 3, wherein the suction line has an intake opening, wherein said tub drain fitting includes an upper chamber portion, a lower chamber portion, a discharge connection portion, and a tub plug which is disposed at a height below said intake opening of the suction line for selectively allowing or blocking fluid communication between said upper chamber portion and said discharge connection portion; said overflow line being connected to said upper chamber portion at a level above that of said tub plug; and said branch line being connected to said tub drain fitting at a level below that of said tub plug.

5. A tub as defined by claim 1, further comprising a shutoff valve for opening or closing said vent opening.

6. A tub as defined by claim 1, wherein the nozzle includes shutoff means for selectively blocking the nozzle dependent upon fluid pressure in the nozzle, to prevent fluid from being introduced from the nozzle into the tub at any fluid pressure up to a predetermined low fluid pressure in the nozzle, and which automatically opens to allow fluid to be introduced from the nozzle into the tub when fluid pressure in the nozzle exceeds said predetermined low fluid pressure; and wherein said shutoff means comprises a shutoff body.

7. A tub as defined by claim 5, wherein the pump has a drive motor having a variable, steplessly regulatable rotational speed; the fluid system further comprising a level sensor for detecting a minimum fill height in the tub which, when said minimum fill height in the tub is exceeded, supplies a signal to cause the drive motor of the pump to be controlled to operate at a pumping capacity that results in a pump pressure below said predetermined low fluid pressure.

8. A tub as defined by claim 1, wherein said means for selectively allowing or blocking fluid communication between said overflow line and the suction line of the pump comprises a first controllable shutoff valve, and further comprising:
a tub drainpipe connected to the closable tub drain fitting for discharging liquid from the fluid system;
a branch line connecting said overflow line to said tub drainpipe;
a second controllable shutoff valve for selectively allowing or blocking fluid communication between said branch line and said tub drainpipe, said second controllable shutoff valve being disposed in said branch line; and
said branch line being connected to said overflow line at a location downstream of the nozzle as viewed in a direction of fluid flow therethrough;
level sensor means for detecting a minimum fill height in the tub which, when said minimum fill height in the tub is exceeded, supplies an output signal;
a first control drive for controlling said first controllable shutoff valve and a second control drive for controlling said second controllable shutoff valve, said first and second control drives being triggerable by said output signal of said level sensor such that, when said minimum fill height is exceeded, said first controllable shutoff valve opens and said second controllable shutoff valve closes at least partially.

9. In a tub including a bottom portion having a drain opening and a fluid system connected to said tub, said fluid system having a pump including a section side and a pressure side and at least one nozzle mounted on said tub; said pressure side being connected to said at least one nozzle for introducing a water-and-air mixture into the interior of the tub, said fluid system further having a drain fitting connected to a circulation inflow line and a pipe drain, the improvement wherein the drain fitting comprises:
a body adapted to be disposed beneath the bottom portion of the tub, said body including an upper chamber portion and a discharge connection portion;
said upper chamber portion having a flow chamber, an upper opening connecting the drain opening of the tub and said flow chamber, and said discharge connection portion having a lower discharge opening connected to the drain pipe;
a valve disk mounted on said body which is actuatable from outside said flow chamber for selectively allowing or blocking fluid communication between said upper chamber and said discharge connection portion; and
said body further including first and second flow openings which are disposed in said flow chamber; said first and second flow openings being disposed above said valve disk, said first flow opening being connected with said inflow line and said second flow opening being connected with said suction line of said pump.

10. A tub as defined by claim 9, wherein said first flow opening has a pipe extension which protrudes into said flow chamber and is oriented in a direction toward said second flow opening.

11. A tub as defined by claim 11, wherein said flow chamber has an interior diameter, and further comprising:
a pipe insert disposed in said flow chamber, said pipe insert having one end which communicates with the drain opening of the tub and at least one flow opening therein disposed on a side thereof which is adjacent said second flow opening; and said pipe insert having a smaller diameter than said interior diameter of said flow chamber.

* * * * *